United States Patent
Bathgate et al.

(10) Patent No.: US 10,081,662 B2
(45) Date of Patent: Sep. 25, 2018

(54) MODIFIED RELAXIN B CHAIN PEPTIDES

(71) Applicant: The Florey Institute of Neuroscience and Mental Health, Parkville (AU)

(72) Inventors: Ross Alexander David Bathgate, Monee Ponds (AU); Mohammed Akhter Hossain, Brunsiwck West (AU); John Desmond Wade, Canterbury (AU)

(73) Assignee: THE FLOREY INSTITUTE OF NEUROSCIENCE AND MENTAL HEALTH, Parkville, Victoria (AU)

( * ) Notice: Subject to any disclaimer, the term of this patent is extended or adjusted under 35 U.S.C. 154(b) by 0 days.

(21) Appl. No.: 15/304,434

(22) PCT Filed: Apr. 17, 2015

(86) PCT No.: PCT/AU2015/050184
§ 371 (c)(1),
(2) Date: Oct. 14, 2016

(87) PCT Pub. No.: WO2015/157829
PCT Pub. Date: Oct. 22, 2015

(65) Prior Publication Data
US 2017/0037106 A1   Feb. 9, 2017

(30) Foreign Application Priority Data
Apr. 17, 2014   (AU) .................. 2014901409

(51) Int. Cl.
| | | |
|---|---|---|
| *C07K 14/00* | (2006.01) |
| *C07K 14/435* | (2006.01) |
| *C07K 14/46* | (2006.01) |
| *C07K 14/47* | (2006.01) |
| *C07K 14/575* | (2006.01) |
| *C07K 14/64* | (2006.01) |
| *C12N 15/00* | (2006.01) |
| *C12N 15/09* | (2006.01) |
| *C12N 15/11* | (2006.01) |
| *C12N 15/12* | (2006.01) |
| *C12N 15/16* | (2006.01) |
| *A61K 38/00* | (2006.01) |

(52) U.S. Cl.
CPC .............. *C07K 14/64* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,326,694 A | * | 7/1994 | Hudson ................. | C07K 14/64 435/320.1 |
| 2011/0130332 A1 | | 6/2011 | Park et al. | |
| 2011/0243942 A1 | | 10/2011 | Wang | |
| 2016/0060322 A1 | | 3/2016 | Narayan et al. | |

FOREIGN PATENT DOCUMENTS

| | | |
|---|---|---|
| CN | 102643825 A | 8/2012 |
| WO | WO-2009055854 A1 | 5/2009 |
| WO | WO-2013007563 A1 | 1/2013 |

OTHER PUBLICATIONS

Tokuriki et al., 2009, Curr. Opin. Struc. Biol. 19:596-604).*
Bhattacharya et al. (2017, PLoS ONE 12(3): e0171355, https://doi.org/10.1371/journal.pone.0171355).*
International Search Report issued PCT/AU2015/050184 on May 27, 2015.
Eigenbrot, et al,. X-ray Structure of Human Relaxin at 1 5 a Comparison to Insulin and Implications for Receptor Binding Determinants, J. Mol. Biol. 1991, 221:15-21.
Haugaard-Kedström, et al., Design, Synthesis, and Characterization of a Single-Chain Peptide Antagonist for the Relaxin-3 Receptor RXFP3, J. Am. Chem. Soc., 2011, 133:4965-4974.
Hossain, et al., The Minimal Active Structure of Human Relaxin-2, The Journal of Biological Chemistry, 2011, 286:43:37555-37565.
Hossain, et al., The Roles of the A- and B-Chains of Human Relaxin-2 and -3 on Their Biological Activity, Current Protein and Peptide Science, 2010, 11(8):719-724.
Silvertown, et al., Analog of H2 Relaxin Exhibits Antagonistic Properties and Impairs Prostate Tumor Growth, The FASEB Journal, 2006, 21(3):754-765.
Supplementary European Search Report issued in EP15780000 on Aug. 31, 2017.

* cited by examiner

Primary Examiner — Elizabeth Kemmerer
(74) Attorney, Agent, or Firm — Blank Rome LLP

(57) ABSTRACT

Provided herein are biologically active single chain relaxin peptides. In particular the present invention relates to single chain relaxin peptides comprising a B chain derived from relaxin-2, the peptide being truncated by one or more amino acid residues at the N-terminus with respect to the sequence of the B chain of native relaxin-2. Typically the single chain relaxin peptides selectively bind to the RXFP1 receptor.

14 Claims, 9 Drawing Sheets
Specification includes a Sequence Listing.

A

B

SEQUENCE LISTING

<160> NUMBER OF SEQ ID NOS: 17

<210> SEQ ID NO 1
<211> LENGTH: 29
<212> TYPE: PRT
<213> ORGANISM: Artificial Sequence
<220> FEATURE:
<223> OTHER INFORMATION: Synthetic sequence

<400> SEQUENCE: 1

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 2
<211> LENGTH: 29
<212> TYPE: PRT
<213> ORGANISM: Artificial Sequence
<220> FEATURE:
<223> OTHER INFORMATION: Synthetic sequence

<400> SEQUENCE: 2

Asp Ser Trp Met Glu Glu Val Ile Lys Leu Ser Gly Arg Glu Leu Val
1               5                   10                  15

Arg Ala Gln Ile Ala Ile Ser Gly Met Ser Thr Trp Ser
            20                  25

<210> SEQ ID NO 3
<211> LENGTH: 33
<212> TYPE: PRT
<213> ORGANISM: Artificial Sequence
<220> FEATURE:
<223> OTHER INFORMATION: Synthetic sequence

<400> SEQUENCE: 3

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser Lys Arg Ser
            20                  25                  30

Leu

<210> SEQ ID NO 4
<211> LENGTH: 33
<212> TYPE: PRT
<213> ORGANISM: Artificial Sequence
<220> FEATURE:
<223> OTHER INFORMATION: Synthetic sequence

<400> SEQUENCE: 4

Asp Ser Trp Met Glu Glu Val Ile Lys Leu Ser Gly Arg Glu Leu Val
1               5                   10                  15

Arg Ala Gln Ile Ala Ile Ser Gly Met Ser Thr Trp Ser Lys Arg Ser
            20                  25                  30

Leu

<210> SEQ ID NO 5
<211> LENGTH: 23
<212> TYPE: PRT
<213> ORGANISM: Artificial Sequence
<220> FEATURE:
<223> OTHER INFORMATION: Synthetic sequence

<400> SEQUENCE: 5

```
Val Ile Lys Leu Cys Gly Arg Glu Leu Val Arg Ala Gln Ile Ala Ile
1               5                   10                  15

Cys Gly Met Ser Thr Trp Ser
            20
```

<210> SEQ ID NO 6
<211> LENGTH: 27
<212> TYPE: PRT
<213> ORGANISM: Artificial Sequence
<220> FEATURE:
<223> OTHER INFORMATION: Synthetic sequence

<400> SEQUENCE: 6

```
Val Ile Lys Leu Cys Gly Arg Glu Leu Val Arg Ala Gln Ile Ala Ile
1               5                   10                  15

Cys Gly Met Ser Thr Trp Ser Lys Arg Ser Leu
            20                  25
```

<210> SEQ ID NO 7
<211> LENGTH: 27
<212> TYPE: PRT
<213> ORGANISM: Artificial Sequence
<220> FEATURE:
<223> OTHER INFORMATION: Synthetic sequence

<400> SEQUENCE: 7

```
Val Ile Lys Leu Ser Gly Arg Glu Leu Val Arg Ala Gln Ile Ala Ile
1               5                   10                  15

Ser Gly Met Ser Thr Trp Ser Lys Arg Ser Leu
            20                  25
```

<210> SEQ ID NO 8
<211> LENGTH: 23
<212> TYPE: PRT
<213> ORGANISM: Artificial Sequence
<220> FEATURE:
<223> OTHER INFORMATION: Synthetic sequence

<400> SEQUENCE: 8

```
Val Ile Lys Leu Ser Gly Arg Glu Leu Val Arg Ala Gln Ile Ala Ile
1               5                   10                  15

Ser Gly Met Ser Thr Trp Ser
            20
```

<210> SEQ ID NO 9
<211> LENGTH: 27
<212> TYPE: PRT
<213> ORGANISM: Artificial Sequence
<220> FEATURE:
<223> OTHER INFORMATION: Synthetic sequence

<400> SEQUENCE: 9

```
Val Ile Lys Leu Ser Gly Arg Glu Leu Val Lys Ala Gln Ile Ala Ile
1               5                   10                  15

Ser Gly Met Ser Thr Trp Ser Lys Arg Ser Leu
            20                  25
```

<210> SEQ ID NO 10
<211> LENGTH: 27
<212> TYPE: PRT
<213> ORGANISM: Artificial Sequence
<220> FEATURE:
<223> OTHER INFORMATION: Synthetic sequence
<220> FEATURE:

```
<221> NAME/KEY: MOD_RES
<222> LOCATION: (11)..(11)
<223> OTHER INFORMATION: homoarginine

<400> SEQUENCE: 10

Val Ile Lys Leu Ser Gly Arg Glu Leu Val Arg Ala Gln Ile Ala Ile
1               5                   10                  15

Ser Gly Met Ser Thr Trp Ser Lys Arg Ser Leu
            20                  25

<210> SEQ ID NO 11
<211> LENGTH: 27
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (11)..(11)
<223> OTHER INFORMATION: norarginine

<400> SEQUENCE: 11

Val Ile Lys Leu Ser Gly Arg Glu Leu Val Arg Ala Gln Ile Ala Ile
1               5                   10                  15

Ser Gly Met Ser Thr Trp Ser Lys Arg Ser Leu
            20                  25

<210> SEQ ID NO 12
<211> LENGTH: 27
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: ACETYLATION

<400> SEQUENCE: 12

Val Ile Lys Leu Ser Gly Arg Glu Leu Val Arg Ala Gln Ile Ala Ile
1               5                   10                  15

Ser Gly Met Ser Thr Trp Ser Lys Arg Ser Leu
            20                  25

<210> SEQ ID NO 13
<211> LENGTH: 27
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: ACETYLATION

<400> SEQUENCE: 13

Val Ile Lys Leu Ser Gly Ala Glu Leu Val Arg Ala Gln Ile Ala Ile
1               5                   10                  15

Ser Gly Met Ser Thr Trp Ser Lys Arg Ser Leu
            20                  25

<210> SEQ ID NO 14
<211> LENGTH: 27
<212> TYPE: PRT
<213> ORGANISM: Artificial Sequence
<220> FEATURE:
<223> OTHER INFORMATION: Synthetic sequence
```

```
<220> FEATURE:
<221> NAME/KEY: MOD_RES
<222> LOCATION: (1)..(1)
<223> OTHER INFORMATION: ACETYLATION

<400> SEQUENCE: 14

Val Ile Lys Leu Ser Gly Arg Glu Leu Val Ala Ala Gln Ile Ala Ile
1               5                   10                  15

Ser Gly Met Ser Thr Trp Ser Lys Arg Ser Leu
            20                  25

<210> SEQ ID NO 15
<211> LENGTH: 27
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: ACETYLATION

<400> SEQUENCE: 15

Val Ile Lys Leu Ser Gly Arg Glu Leu Val Arg Ala Gln Ala Ala Ile
1               5                   10                  15

Ser Gly Met Ser Thr Trp Ser Lys Arg Ser Leu
            20                  25

<210> SEQ ID NO 16
<211> LENGTH: 27
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: ACETYLATION

<400> SEQUENCE: 16

Val Ile Lys Leu Ser Gly Ala Glu Leu Val Ala Ala Gln Ala Ala Ile
1               5                   10                  15

Ser Gly Met Ser Thr Trp Ser Lys Arg Ser Leu
            20                  25

<210> SEQ ID NO 17
<211> LENGTH: 27
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: ACETYLATION

<400> SEQUENCE: 17

Val Ile Lys Leu Ser Gly Arg Glu Leu Val Arg Ala Gln Ile Ala Ile
1               5                   10                  15

Ser Gly Met Ser Thr Trp Ser Lys Lys Lys Lys
            20                  25
```

US 10,081,662 B2

MODIFIED RELAXIN B CHAIN PEPTIDES

This application is the U.S. national stage of International Patent Application No. PCT/AU2015/050184, filed Apr. 17, 2015, which claims the benefit of Australian Patent Application No. 2014901409, filed Apr. 17, 2014.

FIELD OF THE INVENTION

The present invention relates generally to biologically active single chain relaxin peptides and to nucleic acids encoding the same. The present invention in particular relates to single chain relaxin-2 peptides comprising a relaxin-2 derived B chain and which optionally selectively bind to the RXFP1 (LGR7) receptor. The invention also relates to uses of peptides of the invention, methods employing the same and to compositions comprising such peptides.

BACKGROUND OF THE INVENTION

Relaxins are heterodimeric peptide hormones composed, in their mature form, of an A chain and a B chain linked via disulfide bridges. Human relaxins in their mature form are typically stabilised by three disulfide bonds, two inter-chain disulfide bonds between the A chain and B chain and one intra-chain disulfide bond between cysteine residues in the A chain.

Relaxins have been conserved through vertebrate evolution and have been characterised in a large and diverse range of vertebrate species. In particular the cysteine residues in the B and A chains responsible for the intra- and inter-chain disulfide bonds are highly conserved. Whilst in most species only two forms of relaxin have been identified (relaxin and relaxin-3), in humans three distinct forms of relaxin have been described and the genes and polypeptides characterised. These have been designated H1, H2 and H3, Homologues of H1 and H2 relaxin have been identified in other higher primates including chimpanzees, gorillas and orangutans. Differing expression patterns for H1, H2 and H3 relaxin suggest some differences in biological roles, however all three forms display similar biological activities, as determined for example by their ability to modulate (stimulate or inhibit) cAMP activity in cells expressing relaxin family receptors, and accordingly share some biological functions in common.

The biological actions of relaxins are mediated through G protein coupled receptors. To date, H1, H2 and H3 relaxins have been shown to primarily recognise and bind four receptors, RXFP1 (LGR7), RXFP2 (LGR8), RXFP3 (GPCR135) and RXFP4 (GPCR142). Receptors RXFP1 and RXFP2 are structurally distinct from receptors RXFP3 and RXFP4, yet despite the differences there is significant cross-reactivity between different native relaxin molecules and different receptors.

Initially thought to be predominantly a reproductive hormone, it has become increasingly clear that human relaxin-2 has pleiotropic actions. Relaxin-2 has been shown to have potent cardioprotective (including vasodilatory and angiogenic) effects and antifibrotic effects (see, for example, Du et al., 2010, *Nat. Rev. Cardiol*, 7, 48-58 and Samuel, 2005, *Clin. Med. Res.* 3, 241-249). Relaxin-2 is currently undergoing clinical trial evaluation for the treatment of acute heart failure.

With the increasing therapeutic promise shown by relaxin-2 and the continued development of potential clinical applications there is also an interest in developing relaxin peptides that are simpler in structure than native relaxin molecules and yet which retain the ability to bind to relaxin receptors and/or retain relaxin-associated biological activity. Simplifying the structure of therapeutic peptides and minimising the amino acid sequence required to impart biological activity on therapeutic peptides can serve to reduce the cost of polypeptide synthesis, reduce the complexity and difficulty of synthesis, and/or improve the efficiency of synthesis. Moreover, simplified, smaller molecules may exhibit improved in vivo activities and/or cellular uptake of such molecules may be improved when compared to native counterparts. In addition, improvements to pharmacokinetic properties (such as half-life, bioavailability etc) and/or therapeutic efficacy may be more readily made to simplified, smaller peptides.

SUMMARY OF THE INVENTION

Provided herein are novel, modified relaxin peptides that comprise only relaxin-2-derived B chain and which retain biological activity associated with native relaxin-2. Peptides of the invention are "modified" in that they possess B chain amino acid sequences that differ from those found in corresponding native relaxin-2 molecules at one or more positions.

A first aspect of the invention provides a biologically active single chain relaxin peptide comprising a relaxin B chain derived from relaxin-2, wherein the peptide is truncated by one or more amino acid residues at the N-terminus with respect to the sequence of the B chain of native relaxin-2.

Typically the native relaxin-2 comprises or consists of the sequence shown in SEQ ID NO: 1.

The peptide may be truncated by, for example, up to about seven residues at the N-terminus. The peptide may comprise or consist of the amino acid sequence shown in SEQ ID NO:5, or a variant or derivative thereof.

The peptide may comprise one or more additional amino acids at the C-terminus. The one or more additional amino acids may increase the solubility of the peptide when compared to the native relaxin-2 B chain. One or more of the additional amino acids may be positively charged amino acids. The peptide may comprise four additional amino acids at the C-terminus. The additional amino acids may be KRSL. The peptide may comprise or consist of the amino acid sequence shown in SEQ ID NO:6, or a variant or derivative thereof.

One or more cysteine residues in the native relaxin-2 sequence may be replaced with a neutral amino acid, for example serine or alanine, more typically serine. For example, the cysteine residues at positions 11 and 23 of the native human relaxin-2 B chain sequence shown in SEQ ID NO:1 may be replaced by serine residues. The peptide may comprise or consist of the amino acid sequence shown in SEQ ID NO:7, or a variant or derivative thereof, or SEQ ID NO:8, or a variant or derivative thereof.

One or more arginine residues of the native human relaxin-2 B chain sequence may be replaced by a basic amino acid. The basic ammo acid may be lysine, or a mimetic or isostere of arginine. Said mimetic or isostere may, for example, be homoarginine, norarginine or guanidine propionic acid. The arginine residue at position 17 of the native human relaxin-2 B chain sequence shown in SEQ ID NO:1 may be replaced by lysine, homoarginine, norarginine or guanidine propionic acid. The peptide may comprise or consist of the amino acid sequence shown in SEQ ID NO:9, or a variant or derivative thereof, SEQ ID NO:10, or a variant or derivative thereof, or SEQ ID NO:11, or a variant or derivative thereof.

The single chain peptide typically comprises a C-terminal amide or acid group, more typically a C-terminal amide group. The single chain peptide may comprise an N-terminal acetyl group.

The peptide may be selective or specific for the RXFP1 receptor. The peptide may be an agonist of the RXFP1 receptor. The peptide may be a selective or specific agonist of the RXFP1 receptor.

A second aspect of the invention provides a polynucleotide encoding a modified biologically active single chain relaxin peptide according to the first aspect.

A third aspect of the invention provides a pharmaceutical composition comprising a biologically active single chain relaxin peptide of the first aspect, or a polynucleotide of the second aspect, optionally together with one or more pharmaceutically acceptable carriers, excipients or diluents.

A fourth aspect provides a method for treating or preventing a disease or condition, the method comprising administering to a subject in need thereof a biologically active single chain relaxin peptide of the first aspect, a polynucleotide of the second aspect or a pharmaceutical composition of the third aspect.

The disease or condition may be fibrosis or a cardiovascular disease or condition. The fibrosis may be renal fibrosis, cardiac fibrosis or pulmonary fibrosis. The cardiovascular disease or condition may be acute heart failure, coronary artery disease, cardiac fibrosis or microvascular disease.

BRIEF DESCRIPTION OF THE DRAWINGS

The present invention is described, by way of non-limiting example only, with reference to the accompanying drawings.

Figure 1:
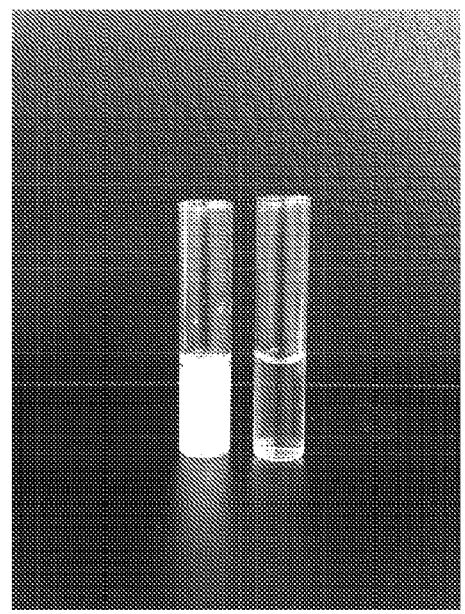
FIG. 1. Solubility of H2 relaxin B chains (at concentration 4 mg/ml). The native H2 B chain is insoluble (left vial), whereas the B7-33 C11.23S peptide is soluble (right vial).

The subject specification contains amino acid sequence information prepared using the programme PatentIn Version 3.5, presented herein in a Sequence Listing. Amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. Sequences of the various peptides are listed in Table 1.

DETAILED DESCRIPTION OF THE INVENTION

The articles "a" and "an" are used herein to refer to one or to more than one (i.e., to at least one) of the grammatical object of the article. By way of example, "an element" means one element or more than one element.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

In the context of this specification, the term "about," is understood to refer to a range of numbers that a person of skill in the art would consider equivalent to the recited value in the context of achieving the same function or result.

The term "peptide" means a polymer made up of amino acids linked together by peptide bonds. The term "polypeptide" may also be used to refer to such a polymer although in some instances a polypeptide may be longer i.e. composed of greater amino acid residues) than a peptide. Nevertheless, the terms "polypeptide" and "peptide" may be used interchangeably herein.

The term "relaxin peptide" as used herein means a peptide, whether modified in accordance with the present invention or corresponding to a naturally occurring relaxin molecule which displays biological activity typically associated with relaxin. The level of such relaxin biological activity displayed by a modified peptide of the invention may be equivalent to that of a naturally occurring or native relaxin, or may be enhanced or reduced when compared with the activity of a naturally occurring or native relaxin. In the context of the present disclosure, the term "single chain relaxin peptide" refers to peptides comprising only a relaxin B chain sequence.

The term "modified" as used herein in the context of a relaxin peptide means a peptide that differs from a naturally occurring or native relaxin peptide at one or more amino acid positions of such naturally occurring or native peptide.

The term "conservative amino acid substitution" as used herein refers to a substitution or replacement of one amino acid for another amino acid with similar properties within a peptide chain. For example, the substitution of the charged amino acid glutamic acid (Glu) for the similarly charged amino acid aspartic acid (Asp) would be a conservative amino acid substitution. The nature of other conservative amino acid substitutions is well known to those skilled in the art.

The term "native" as used herein in relation to relaxin peptides refers to naturally occurring or wild-type molecules. In various contexts the terms "native" and "naturally occurring" may refer to a relaxin peptide as encoded by, and produced from, the genome of an organism. For example in the context of the present disclosure, the term "native human relaxin-2" or "native H2 relaxin" refers to the native or naturally occurring human relaxin-2 molecule, being a heterodimer comprising an A and a B chain. The amino acid of the B chain of native H2 relaxin may be as shown in SEQ ID NO:1. The term "native" also refers to various alternative forms (e.g. post-translationally modified) in which the naturally occurring or wild-type molecule may be found, and the term "native" encompasses such alternative forms.

As used herein the term "derived" in the context of B chains in modified peptides means that the B chain sequence corresponds to, originates from, or otherwise shares significant sequence homology with a naturally occurring relaxin B chain sequence. Those skilled in the art will understand that by being "derived" from a naturally occurring or native relaxin sequence, the sequence in the modified peptide need not be physically constructed or generated from the naturally occurring or native sequence, but may be chemically synthesised such that the sequence is "derived" from the naturally occurring or native sequence in that it shares sequence homology and function with naturally occurring or native sequence.

As used herein the term "selective" when used in the context of the ability of a modified relaxin peptide to bind a particular receptor, for example the RXFP1 (LGR7) receptor, means that the peptide binds that receptor at significantly higher frequency than it binds other receptors, for example the RXFP2 receptor. A modified relaxin peptide that is "specific" for a particular receptor is one that possesses no discernable activity at any other receptor. Thus, a modified relaxin polypeptide that is "specific" for RXFP1 is, by definition, selective for RXFP1.

The term "polynucleotide" as used herein refers to a single- or double-stranded polymer of deoxyribonucleotide, ribonucleotide bases or known analogues of natural nucleotides, or mixtures thereof, that encodes a peptide or polypeptide. The term includes reference to the specified sequence as well as to the sequence complimentary thereto, unless otherwise indicated. The terms "polynucleotide" and "nucleic acid" may be used interchangeably herein.

As used herein the terms "treating", "treatment", "preventing" and "prevention" refer to any and all uses which remedy a condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery. Similarly, "prevention" dose not necessarily mean that the subject will not eventually contract a particular condition or disease. Rather, "prevention" encompasses reducing the severity of, or delaying the onset of, a particular condition or disease. In the context of some conditions, methods of the present invention involve "treating" the condition in terms of reducing or eliminating the occurrence of a highly undesirable and irreversible outcome of the progression of the condition but may not of itself prevent the initial occurrence of the condition. Accordingly, treatment and prevention include amelioration of the symptoms of a particular condition or preventing or otherwise reducing the risk of developing a particular condition.

As used herein the terms "effective amount" and "effective dose" include within their meaning a non-toxic but sufficient amount or dose of an agent or compound to provide the desired effect. The exact amount or dose required will vary from subject to subject depending on factors such as the species being treated, the age and general condition of the subject, the severity of the condition being treated, the particular agent being administered and the mode of administration and so forth. Thus, it is not possible to specify an exact "effective amount" or "effective dose". However, for any given case, an appropriate "effective amount" or "effective dose" may be determined by one of ordinary skill in the art using only routine experimentation.

Human relaxin-2 (H2 relaxin) is an insulin-like peptide, comprising two chains (A and B chains) and three disulfide bonds. The A chain contains 24 residues whereas the B chain may have length variations (B1-29, B1-31 and B1-33) at the C-terminus. The recombinant H2 relaxin currently under human clinical trials (Serelaxin; RLX030) for the treatment of acute heart failure contains 29 residues in the B-chain. In the context of the present specification, this B1-29 containing H2 relaxin is referred to as "native H2 relaxin" or "native human relaxin-2", and the B1-29 B chain is referred to as "native H2 relaxin B chain" or "native human relaxin-2 B chain". A typical amino acid sequence of the native H2 relaxin B chain is shown in SEQ ED NO:1.

This native H2 relaxin B chain (SEQ ID NO:1) has an overall net charge of zero (four positively charged and four negatively charged amino acids) and is insoluble in aqueous solution, making chemical synthesis and purification difficult. In contrast, an extended B chain sequence with an additional four amino acids (KRSL) at the C-terminus (B1-33) has an overall charge of +2 (six positively charged and four negatively charged amino acids), thereby imparting improved solubility compared with the native H2 relaxin B chain. Once the B chain (either native or B1-33) is chemically combined with the A chain with three-disulfide connectivity, the resulting H2 relaxin molecules become very soluble. However the cost and efficiency, inter alia, of synthesis of a heterodimeric molecule is a hindrance to the large scale production of native relaxin-2 for therapeutic purposes and for the formulation of suitable pharmaceutical compositions.

As described and exemplified herein the present inventors have synthesised modified, single relaxin B chain peptides that are soluble and retain biological activity associated with relaxin-2. In particular embodiments these peptides are shorter than the native relaxin-2 B chain. Accordingly, being considerably simpler in structure, the peptides of the present invention offer numerous advantages for over longer relaxin molecules and over the native relaxin-2 molecule in terms of production of molecules and pharmaceutical composition formulation.

Provided herein are modified, single chain relaxin peptides possessing biological activity associated with relaxin-2, and that are optionally capable of selectively or specifically binding and activating the RXFP1 receptor. According to one aspect of the present invention, there is provided biologically active single chain relaxin peptides comprising a relaxin B chain derived from relaxin-2, wherein the peptides are truncated by one or more amino acid residues at the N-terminus with respect to the sequence of the B chain of native relaxin-2. In particular, provided herein are single chain peptides truncated by up to about 7 amino acids at the N-terminus of the relaxin-2 B chain compared to the native relaxin-3 B chain sequence, and optionally incorporating up to about 4 additional amino acids at the C-terminus. Optionally the peptides also comprise one or more amino acid modifications within the peptide chain replacing, for example, cysteine residue(s) with neutral amino acids, and/or replacing arginine residue(s) with mimetics or isosteres.

The truncation of relaxin peptides, the addition of amino acids and the replacement of amino acid residues may be achieved in any one of a number of ways as will be apparent to those skilled in the art, using approaches and methodologies well known to those skilled in the art.

The single B chain relaxin peptides of the present invention do not include a relaxin- or relaxin superfamily member-derived A chain. However those skilled in the art will appreciate that the term "single B chain relaxin peptide", and variations thereof, simply refers to the absence of an A chain. Peptides of the present disclosure may be combined with or linked to (by covalent or other means) one or more additional proteinaceous or non-proteinaceous moieties as may be desirable depending on the use to which the relaxin peptide of the invention is to be put.

The B chain of native H2 relaxin comprises the amino acid sequence depicted in SEQ ID NO.1. Accordingly, the B chain amino acid sequences of single chain relaxin peptides the subject of the present invention may be based on, or derived from, the amino acid sequence of the H2 relaxin B chain, for example the sequence depicted in SEQ ID NO:2. However those skilled in the art will also appreciate that the amino acid sequences of B chains from which the modified peptides of the invention may be based, or from which the modified peptides may be derived, may include variants of this H2 relaxin B chain sequence.

The term "variant" as used herein refers to substantially similar sequences. Generally, peptide sequence variants also possess qualitative biological activity in common, such as receptor binding activity. Further, these peptide sequence variants may share at least 50%, 55%, 60%, 65%, 70%, 75%, 80%, 85%, 90%, 91%, 92%, 93%, 94%, 95%, 96%, 97%, 98% or 99% sequence identity. Also included within the meaning of the term "variant" are homologues of peptides of the invention. A homologue is typically a peptide from a different species but sharing substantially the same biological function or activity as the corresponding peptide disclosed herein. Further, the term "variant" also includes analogues of the peptides of the present invention, wherein the term "analogue" means a peptide which is a derivative of a peptide of the invention, which derivative comprises addition, deletion, substitution of one or more amino acids, such that the peptide typically retains substantially the same function, for example in terms of receptor binding activity. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in a peptide although random insertion is also possible with suitable screening of the resulting product. Deletional variants are characterised by the removal of one or more amino acids from the sequence. Substitutional amino acid variants are those in which at least one residue in a sequence has been removed and a different residue inserted in its place. Additions to amino acid sequences may include fusions with other peptides, polypeptides, proteins or polymers. Modifications may be made to relaxin polynucleotide sequences, for example via the insertion or deletion of one or more codons, such that modified derivatives of the relaxin polypeptide are generated. Such modifications are also included within the scope of the term "variant". For example, modifications may be made so as to enhance the biological activity or expression level of the relaxin or to otherwise increase the effectiveness of the peptide to achieve a desired outcome.

Single B chain peptides of the invention are modified with respect to the native H2 relaxin sequence such that the peptide sequence is truncated by one or more amino acids at the N-terminus. For example, one, two, three, four, five, six, seven or more amino acids may be deleted from the N-terminus provided the resulting peptide retains biological activity in common with native relaxin-2, for example in terms of RXFP1 receptor binding and activation activity. Similarly, single B chain peptides of the invention may be modified with respect to the native H2 relaxin sequence such that the peptide sequence comprises one or more additional amino acids at the C-terminus. For example, one, two, three, four, or more amino acids may be added to the C-terminus provided the resulting peptide retains biological activity in common with native relaxin-2, for example in terms of RXFP1 receptor binding and activation activity.

One or more cysteine residues in the native relaxin-2 sequence may be replaced by neutral amino acids, such as serine or alanine residues, more typically serine. In a particular embodiment, where the cysteine residues at positions 11 and 23 (or corresponding positions) of the native human relaxin-2 sequence are replaced by serine residues. The single chain polypeptide may further comprise the replacement of one or more arginine residues in the native relaxin-2 sequence with one or more basic amino acids. The basic amino acid may be lysine, or a mimetic or isostere of arginine, such as, for example homoarginine, norarginine or guanidine propionic acid. In a particular embodiment the arginine residue at position 17 of the native human relaxin-2

B chain sequence is replaced by lysine, homoraginine, norarginine or guanidine propionic acid.

The single B chain peptides of the invention typically comprises an amide (for example —NH$_2$) or acid (for example —OH) group on the exposed end of the C-terminal amino acid residue. In particular embodiments this C-terminal group is an amide group, typically NH$_2$.

As described and exemplified herein a single B chain relaxin peptide in accordance with the present invention may comprise or consist of an amino acid sequence as set forth in any one of SEQ ID Nos 5 to 11, or a variant or derivative thereof. Those skilled in the art will however appreciate and recognise that the scope of the present disclosure is not limited to the specific single B chain relaxin peptide sequences exemplified herein, but rather other sequences having the general sequence characteristics set our herein are also contemplated and encompassed.

Therefore, those skilled in the art will appreciate that amino acid sequence modifications additional to these specifically exemplified herein may also be made. Exemplary amino acid changes may include: the replacement of the isoleucine residue at position 20 of the native H2 relaxin B chain sequence of SEQ ID NO:1 with a mimetic or isostere thereof; the replacement of one or more amino acids with non-native amino acid equivalents such as beta-alanine in place of alanine); and the replacement of non helix-inducing residues (such as valine or proline) with helix-inducing native or non-native amino acids (Ala, Aib etc).

The present inventors have previously demonstrated that mutations of arginine residues at positions 13 and 17 in the B chain of relaxin-2 can generate an RXFP1 antagonist peptide (Hossain M A et at. 2010 *Amino Acids* 39::409-16; Silvertown et al. 2007 *FASEB J.* 21:754-65). Accordingly, embodiments of the present invention provide antagonists of RXFP1 wherein peptides disclosed herein contain mutations at positions Arg13 or Arg17 of the native human relaxin-2 B chain sequence shown in SEQ ID NO:1. The arginine residues may be replaced by, for example, lysine residues or arginine mimetics. By way of example, the single B chain peptide B7-33 exemplified herein may be modified by replacing the Arg13 residue with a lysine residue or an arginine mimetic or isostere such as homoarginine.

Relaxin peptides further modified at the N- and/or C-terminus by the addition, deletion or substitution of one or more amino acid residues also fall within the scope of the present invention. Such modifications may, for example, improve the solubility of the peptide. For example, the C-terminus may be extended by the addition of, or two or more C-terminal residues may be replaced with, two or more charged residues such as KK, RR or KR.

Such amino acid changes may be effected by synthesis of peptide sequences (such as, but not limited to the method exemplified herein). Alternatively, recombinant DNA and nucleotide replacement techniques may be used which include the addition, deletion or substitution of nucleotides (conservative and/or non-conservative), under the proviso that the proper reading frame is maintained. A conservative substitution denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted amino acid in place of an unsubstituted parent amino acid. Exemplary techniques for generating such amino acid insertion, deletion or substitution modifications include random mutagenesis, site-directed mutagenesis, oligonucleotide-mediated or polynucleotide-mediated mutagenesis, deletion of selected region(s) through the use of existing or engineered restriction enzyme sites, and the polymerase chain reaction. Such techniques will be well known to those skilled in the art.

Peptides of the invention can also be further modified, for instance, by glycosylation, amidation, carboxylation, or phosphorylation, or by the creation of acid addition salts, amides, esters, in particular C-terminal esters, and N-acyl derivatives. The peptides can also be further modified to create peptide derivatives by forming covalent or non-covalent complexes with other moieties. Covalently-bound complexes can be prepared by cross-linking the chemical moieties to functional groups on the side chains of amino acids comprising the peptides, or at the N-or C terminus. For example, as peptide sequence minimisation may be accompanied by increased susceptibility to enzymatic attack and degradation with a corresponding decrease in plasma half life and in vivo activity, a modified peptide of the present invention may be generated with a polyethylene moiety conjugated at one or more locations (PECiylation) to increase in vivo half life of the peptide. Those skilled in the art will appreciate that a number of other well known approaches exist to extend the in vivo half life of peptides, such as for example the addition of albumin affinity tags, lipidation (fatty acid conjugation), XTENylation, PASylation, oligomerization and the present disclosure is not limited by reference to the exemplary means specifically discussed herein.

The structures of the peptides of the invention may be stabilised through amino acid modifications and subsequent reactions to, for example, induce intra-peptide bonds which may or may not increase potency of the peptide. Some embodiments of the invention provide for alterations of the structure of the peptides including, by way of example only, by head to tail cyclization through amide bonds using appropriate spacer and side-chain to side-chain cyclization and "stapling" through bonds, including but not limited to lactam bonds, disulfide bonds, thioether bonds, or diselenide bonds. Methods for generating such structures are well known to those skilled in the art.

Further, the peptides of the present invention can be conjugated to a reporter group, including, but not limited to a radiolabel, a fluorescent label, an enzyme (e.g., that catalyzes a colorimetric or fluorometric reaction), a substrate, a solid matrix, or a carrier (e. g., biotin or avidin). These are merely exemplary additional modifications that may be made to the modified peptides of the invention. Those skilled in the art will appreciate that further modifications may also be made so as to generate analogues of the peptides of the invention. By way of example only, illustrative analogues and processes for preparing the same are described in International patent application published as WO 2004/113381, the disclosure of which is incorporated herein by reference in its entirety.

Amino acid additions may also result from the fusion of a relaxin peptide or fragment thereof with a second peptide, such as a polyhistidine tag, maltose binding protein fusion, glutathione S transferase fusion, green fluorescent protein fusion, or the addition of an epitope tag such as FLAG or c-myc.

Peptides of the invention may be synthesised by standard methods of liquid or solid phase chemistry well known to those of ordinary skill in the art. For example such molecules may be synthesised following the solid phase chemistry procedures of Steward and Young (Steward, J. M. & Young, J. D., Solid Phase Peptide Synthesis. (2nd Edn.) Pierce Chemical Co., Illinois, USA (1984), or Howl (ed.) *Peptide Synthesis and Applications, Methods in Molecular Biology* (Volume 298), 2005. In general, such synthesis methods comprise the sequential addition of one or more amino acids or suitably protected amino acids to a growing peptide chain. Typically, either the amino or carboxyl group of the first amino acid is protected by a suitable protecting group. The protected amino acid is then either attached to an inert solid support or utilised in solution by adding the next amino acid in the sequence having the complimentary (amino or carboxyl) group suitably protected and under conditions suitable for forming the amide linkage. The protecting group is then removed from this newly added amino acid residue and the next (protected) amino acid is added, and so forth. After all the desired amino acids have been linked, any remaining protecting groups, and if necessary any solid support, is removed sequentially or concurrently to produce the final polypeptide.

Peptides of the invention may also be produced using standard techniques of recombinant DNA and molecular biology that are well known to those skilled in the art. Guidance may be obtained, for example, from standard texts such as Sambrook et al., *Molecular Cloning: A Laboratory Manual*, Cold Spring Harbor, N.Y., 1989 and Ausubel et al., *Current Protocols in Molecular Biology*, Greene Publ. Assoc. and Wiley-Intersciences, 1992, Methods described in Morton et al., 2000 (*Immumnol Cell Biol* 78:603-607), Ryan et al., 1995 (*J Biol Chem* 270:22037-22043) and Johnson et al., 2005 (*J Biol Chem* 280:4037-4047) are examples of suitable purification methods for relaxin peptides, although the skilled addressee will appreciate that the present invention is not limited by the method of purification or production used and any other method may be used to produce relaxin peptides for use in accordance with the methods and compositions of the present invention.

Relaxin peptide fragments may be produced by digestion of a polypeptide with one or more proteinases such as endoLys-C, endoArg-C, endoGlu-C, and staphylococcus V8-protease. The digested peptide fragments can be purified by, for example, high performance liquid chromatographic (HPLC) techniques. The purification of modified relaxin polypeptides of the present disclosure may be scaled-up for large-scale production purposes. For this purpose a range of techniques well known to those skilled in the art are available.

Embodiments of the present disclosure also provide isolated polynucleotides encoding relaxin peptides of the invention. Those skilled in the art will appreciate that heterologous expression of polypeptides may be improved by optimising the codons for the particular species in which the relaxin polypeptide is to be expressed. Accordingly, polynucleotides encoding relaxin peptides of the invention may be codon-optimised for expression in a particular species.

In particular embodiments, polynucleotides may be cloned into a vector. The vector may be a plasmid vector, a viral vector, or any other suitable vehicle adapted for the insertion of foreign sequences, their introduction into eukaryotic cells and the expression of the introduced sequences. Typically the vector is a eukaryotic expression vector and may include expression control and processing sequences such as a promoter, an enhancer, ribosome binding sites, polyadenylation signals and transcription termination sequences.

The present invention also provides antibodies that selectively bind to the modified relaxin peptides of the invention, as well as variants, fragments and analogues thereof. Suitable antibodies include, but are not limited to polyclonal, monoclonal, chimeric, humanised, single chain. Fab fragments, and an Fab expression library. Antibodies of the present invention may act as agonists or antagonists of relaxin polypeptides, or fragments or analogues thereof. Methods for the generation of suitable antibodies will be readily appreciated by those skilled in the art. For example, an anti-relaxin monoclonal antibody, typically containing Fab portions, may be prepared using the hybridoma technology described in Antibodies-A Laboratory Manual, Harlow and Lane, eds., Cold Spring Harbor Laboratory, N.Y. (1988).

Screening for the desired antibody can also be accomplished by a variety of techniques known in the art. Assays for immunospecific binding of antibodies may include, but are not limited to, radioimmunoassays. ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and immunoelectrophoresis assays, and the like (see, for example, Ausubel et al., eds, 1994, Current Protocols in Molecular Biology, Vol. 1, John Wiley & Sons, Inc., New York). Antibody binding may be detected by virtue of a detectable label on the primary anti-relaxin antibody. Alternatively, the anti-relaxin antibody may be detected by virtue of its binding with a secondary antibody or reagent which is appropriately labelled. A variety of methods are known in the art for detecting binding in an immunoassay and are within the scope of the present invention.

Single B chain relaxin peptides of the present invention find particular application as in the study of relaxin biological activities and as therapeutic agents. Polynucleotides encoding the peptides and antibodies to the peptides find similar application. Therapeutic applications include, but are not limited to, the treatment of fibrosis and fibrotic disorders and of cardiovascular disorders. For example, peptides of the invention may find application in the treatment of renal fibrosis, pulmonary fibrosis, cardiac fibrosis, coronary artery disease, acute heart failure, microvascular disease, preeclampsia, hypertensive diseases, scleroderma, cervical ripening, fibromyalgia and in orthodontics. However those skilled in the art will appreciate that the scope of the present disclosure is not limited to these uses, and peptides of the invention will find application in the treatment of any disease, condition or disorder against which native relaxin-2 may be considered.

In general, suitable compositions for use with the methods of the invention may be prepared according to methods and procedures that are known to those of ordinary skill in the art and accordingly may include pharmaceutically acceptable carriers, diluents and/or adjuvants.

Compositions may be administered by standard routes. In general, the compositions may be administered by the parenteral (e.g., intravenous, intraspinal, subcutaneous or intramuscular), oral or topical route. Administration may be systemic, regional or local. The particular route of administration to be used in any given circumstance will depend on a number of factors, including the nature of the condition to be treated, the severity and extent of the condition, the required dosage of the particular compound to be delivered and the potential side-effects of the compound.

In general, suitable compositions may be prepared according to methods which are known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysilloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

Compositions may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may incorporate any suitable surfactant such as an anionic, cationic or non-ionic surfactant such as sorbitan esters or polyoxyethylene derivatives thereof Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

For the purposes of the present invention administration may be therapeutic or preventative. In therapeutic applications, compositions are administered to a patient already suffering from a disease, in an amount sufficient to cure or at least partially arrest the disease and its complications. The composition should provide a quantity of the molecule or agent sufficient to effectively treat the patient. The therapeutically effective dose level for any particular patient will depend upon a variety of factors including: the disorder being treated and the severity of the disorder; activity of the molecule or agent employed; the composition employed; the age, body weight, general health, sex and diet of the patient; the time of administration; the route of administration; the rate of sequestration of the molecule or agent; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases and conditions. Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 $m^2$. Generally, an effective dosage is expected to be in the range of about 25 to about 500 $mg/m^2$, preferably about 25 to about 350 $mg/m^2$, more preferably about 25 to about 300 $mg/m^2$, still more preferably about 25 to about 250 $mg/m^2$, even more preferably about 50 to about 250 $mg/m^2$, and still even more preferably about 75 to about 150 $mg/m^2$.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

Those skilled in the art will appreciate that in accordance with the methods of the present disclosure relaxin peptides may be administered alone or in conjunction with one or more additional agents. Additionally, the present disclosure contemplates combination therapy using relaxin peptides disclosed herein in conjunction with other therapeutic approaches to the treatment of diseases and disorders. For such combination therapies, each component of the combination therapy may be administered at the same time, or sequentially in any order, or at different times, so as to provide the desired effect. Alternatively, the components may be formulated together in a single dosage unit as a combination product. When administered separately, it may be preferred for the components to be administered by the same route of administration, although it is not necessary for this to be so.

Embodiments of the present invention also contemplate the administration of a polynucleotide encoding a single B chain relaxin peptide of the invention. In such situations the polynucleotide is typically operably-linked to a promoter such that the appropriate peptide sequence is produced following administration of the polynucleotide to the subject. The polynucleotide may be administered to subjects in a vector. The vector may be a plasmid vector, a viral vector, or any other suitable vehicle adapted for the insertion of foreign sequences, their introduction into eukaryotic cells and the expression of the introduced sequences. Typically the vector is a eukaryotic expression vector and may include expression control and processing sequences such as a promoter, an enhancer, ribosome binding sites, polyadenylation signals and transcription termination sequences. The nucleic acid construct to be administered may comprise naked DNA or may be in the form of a composition, together with one or more pharmaceutically acceptable carriers.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

Example 1

Single Chain Relaxin-2 Peptide Construction

The amino acid sequences of single B chain relaxin-2 molecules according to the present invention are shown in Table 1. The sequences are also provided in the formal Sequence Listing appearing at the end of this specification under the SEQ ID Nos indicated in the table.

TABLE 1

Amino acid sequences of relaxin-2 B chains. Residues in bold replace cysteine residues at positions 11 and 23 in native human relaxin-2 B chain (SEQ ID NO: 1). Amino acids added to the C-terminus of the native relaxin-2 peptide are underlined. Residues replacing the arginine residue at position 17 of native human relaxin-2 B chain (SEQ ID NO: 1) are double underlined. Ac- indicates N-terminal acetylation of the peptide.

| SEQ ID NO: | Peptide | Sequence |
|---|---|---|
| 1 | H2 B chain | DSWMEEVIKLCGRELVRAQIAICGMSTWS-NH$_2$ |
| 2 | B1-29 C11.23S | DSWMEEVIKLSGRELVRAQIAISGMSTW-NH$_2$ |
| 3 | B1-33 | DSWMEEVIKLCGRELVRAQIAICGMSTWSKRSL-NH$_2$ |
| 4 | B1-33 C11.23S | DSWMEEVIKLSGRELVRAQIAISGMSTWSKRSL-NH$_2$ |
| 5 | B7-29 | VIKLCGRELVRAQIAICGMSTWS-NH$_2$ |
| 6 | Native B7-33 | VIKLCGRELVRAQIAICGMSTWSKRSL-NH$_2$ |
| 7 | Modified B7-33 (B7-33 C11.23S) | VIKLSGRELVRAQIAISGMSTWSKRSL-NH$_2$ |
| 8 | B7-29 C11.23S | VIKLSGRELVRAQIAISGMSTWS-NH$_2$ |
| 9 | B7-33 C11.23S R17K | VIKLSGRELVKAQIAISGMSTWSKRSL-NH$_2$ |
| 10 | B7-33 C11.23S R17HR | VIKLSGRELVhRAQIAISGMSTWSKRSL-NH$_2$ |
| 11 | B7-33 C11.23S R17NR | VIKLSGRELVnRAQIAISGMSTWSKRSL-NH$_2$ |
| 12 | AcB7-33 C11.23S | Ac-VIKLSGRELVRAQIAISGMSTWSKRSL-NH$_2$ |

TABLE 1-continued

Amino acid sequences of relaxin-2 B chains. Residues in bold replace cysteine residues at positions 11 and 23 in native human relaxin-2 B chain (SEQ ID NO: 1). Amino acids added to the C-terminus of the native relaxin-2 peptide are underlined. Residues replacing the arginine residue at position 17 of native human relaxin-2 B chain (SEQ ID NO: 1) are double underlined. Ac- indicates N-terminal acetylation of the peptide.

| SEQ ID NO: | Peptide | Sequence |
|---|---|---|
| 13 | R13A (AcB7-33 C11.23S) | Ac-VIKLSGAELVRAQIAISGMSTWSKRSL-NH₂ |
| 14 | R17A (AcB7-33 C11.23S) | Ac-VIKLSGRELV<u><u>A</u></u>AQIAISGMSTWSKRSL-NH₂ |
| 15 | I20A (AcB7-33 C11.23S) | Ac-VIKLSGRELVRAQAAISGMSTWSKRSL-NH₂ |
| 16 | R13/17A I20A (AcB7-33 C11.23S) | Ac-VIKLSGAELV<u><u>A</u></u>AQAAISGMSTWSKRSL-NH₂ |
| 17 | KKKK (AcB7-29 C11.23S) | Ac-VIKLSGRELVRAQIAISGMSTWS<u>KKKK</u>-NH₂ |

1 hR = homoarginine
2 nR = norarginine

Solid-Phase Peptide Synthesis:

Synthetic single chain relaxin-2 B chain peptides were generated by solid phase peptide synthesis. The synthesis of derivatives of human relaxin-2 B chain was achieved using Fmoc-methodology as previously described (Dawson et al. *J Peptide Res* 53:542-547, 1999) with or without using microwave energy. The solid support was Fmoc-PAL PEG-PS (PerSeptive Biosystems, USA), and HBTU-activated Fmoc-amino acids were used throughout. Fmoc deprotection was with 20% piperidine in DMF. All derivatives were purchased from Auspep (Melbourne, Australia). Cleavage of the peptides from the solid support and side chain deprotection was achieved by a 2 hour treatment with trifluoroacetic acid (ITA) in the presence of phenol, thioanisole, ethanedithiol and water (82.5/5/5/2.5/5, v/v). The crude peptides were subjected to reversed-phase high performance liquid chromatography (RP-HPLC) on a Vydac C18 column (Hesperia, USA) using a 1%/min gradient of CH3CN in 0.1% aqueous TEA for analysis. Some polypeptides were oxidised in a buffer containing 1 mM DPDS for 1 hour and the reaction monitored on HPLC and by mass spectrometry.

Peptide Characterization

Polypeptides were purified using RP-HPLC systems using a preparative column while the final purity of individual synthetic peptides was assessed by analytical RP-HPLC using a Vydac C18 column (250×4.6 mm, 300 Å, 5 µm) with a buffer system of 0.1% trifluoroacetic acid in water (buffer A) and 0.1% trifluoroacetic acid in acetonitrile (buffer B). The molecular weights of all analogues were determined by MAIDI-TOF mass spectrometry using a Bruker AutoflexII instrument in the linear mode at 19.5 kV. Furthermore, the peptide content for each analogue was quantitated by amino acid analysis using vapour-phase acid hydrolysis in 6 M hydrochloric acid containing 2% phenol at 110° C. over 24 hours. The hydrolysate was then converted to stable, fluorescent derivatives using a Waters AccQTag kit. The derivitized amino acids were separated using a Shim-Pak XR ODS column (3×75 mm, 2.2 µm) on a Shimadzu microbore RP-HPLC system.

The inventors have previously shown that truncation of six residues from the N-terminus of the native relaxin-2 B chain (SEQ ID NO:1) does not affect RXFP1 activity indicating that these residues are not functionally important. Truncation of six residues (including three negatively charged amino acids and three hydrophobic residues) from the N-terminus of the native relaxin-2 B chain provides the resulting B chain peptide, (B7-29; SEQ ID NO:5), with an overall positive charge (+3) and improved aqueous solubility. Truncation of six residues from the N-terminus of the native relaxin-2 B chain together with addition of four residues (two positively charged) at the C-terminus yields the peptide, B7-33 (SEQ ID NO:6), with an overall positive charge (+5), and fewer hydrophobic residues. This highly charged peptide is freely water-soluble (FIG. 1).

Example 2

Ligand Binding Activities and cAMP Response Stimulation

Figure 2:
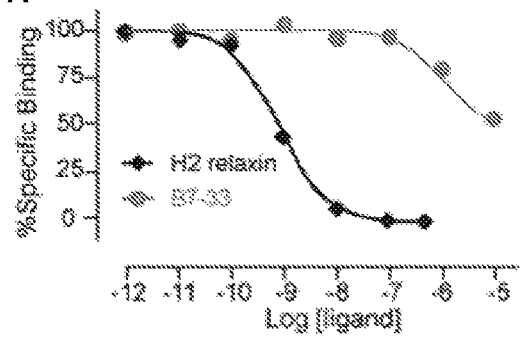
FIG. 2. Binding of native H2 relaxin and single B chain B7-33 C11.23S peptide (B7-33) to RXFP1-expressing cells (A) and to 7BP cells (B) in the presence of europium (Eu)-labelled H2 relaxin.
Figure 2:
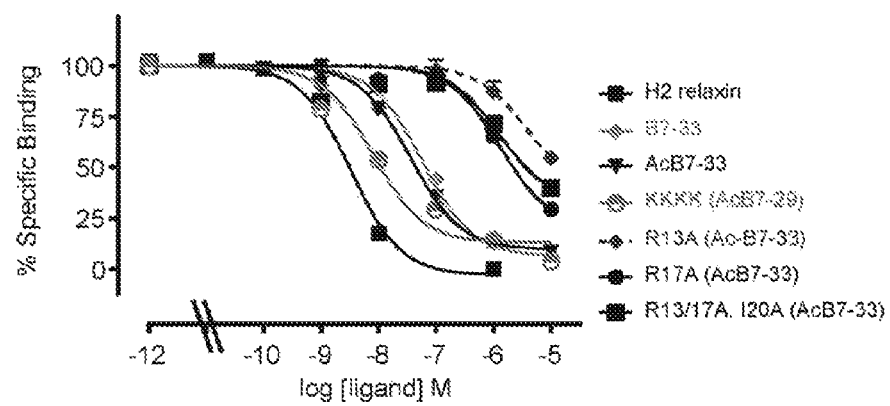

Human embryonic kidney (HEK-293T) cells stably transfected with RXFP1 were cultured in RPMI 1640 medium supplemented with 10% fetal calf serum, 100 µg/ml penicillin, 100 µg/ml streptomycin and 2 mM L-glutamine and plated into 96-well pre-coated with poly-L-lysine for whole cell binding assays. Competition binding experiments were conducted with $Eu^{3+}$-labelled H2 relaxin (as per Shabanpoor et al., 2012, *Biochem Biophys Res Commun.* 420, 253-256) in the absence or presence of increasing concentrations of unlabelled relaxin-2 B chain derivatives. Nonspecific binding was determined with an excess of unlabelled peptides (500 nM H2 relaxin). Fluorescent measurements were recorded at an excitation wavelength of 340 nm and emission of 614 nm on a Victor plate reader (Perkin-Elmer Inc.). FIG. 2A demonstrates that B7-33 C11.23S binds RXFP1, but with lower affinity than H2 relaxin. Binding of native B7-33, B7-33 C11.23S and N-terminal acetylated B chain peptide derivatives to cells expressing a fusion protein comprising the extracellular domain of RXFP1 and the transmembrane domain of CD8 (7BP cells) demonstrates that the B chain peptide derivatives strongly bind to 7BP cells, however still with a lower affinity than H2 relaxin (Table 2, FIG. 2B). Statistical differences in $pIC_{50}$ values were analyzed using one-way analysis of variance coupled to Newman Keul's multiple comparison test for multiple group comparisons in GraphPad Prism 6.

Figure 3:
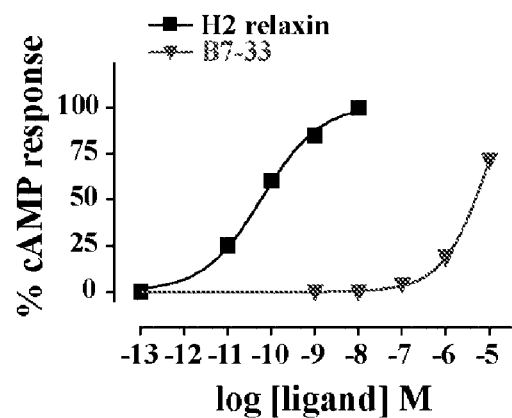
FIG. 3. (A) cAMP-stimulating activity of single chain B7-33 C11.23S peptide (B7-33; inverted triangles) compared to native H2 relaxin (H2 relaxin; squares) in RXFP1-expressing cells. (B) cAMP-stimulating activity of single chain B7-33 C11.23S peptide (B7-33; inverted triangles) compared to native H2 relaxin (H2 relaxin; squares) and the native ligand of RXFP2 INSL3 (diamonds) in RXFP2-expressing cells.
Figure 3:
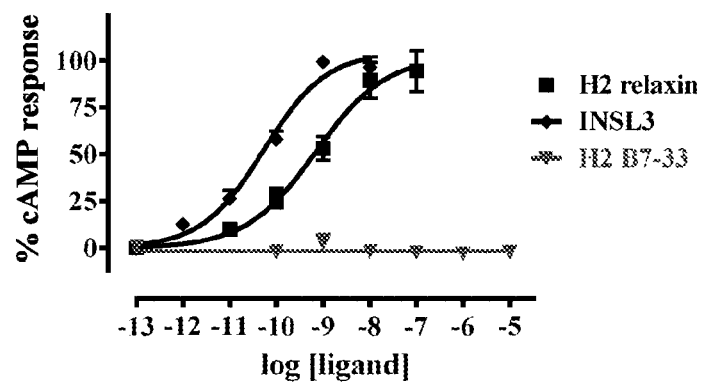

The ability of the relaxin-2 B chain peptide derivatives generated in Example 1 to stimulate cAMP response was also evaluated, using a cAMP reporter gene assay as described previously (Scott et al., 2006, *J Biol Chem.* 281, 34942-34954). HEK-293T cells co-transfected with either RXFP1 or RXFP2, or 7BP cells, and a pCRE β-galactosidase reporter plasmid were plated in 96-well plates. After 24 hours, the co-transfected cells were incubated with increasing concentrations of peptides in parallel to 10 nM of H2 relaxin or INSL3 for RXFP1- or RXFP2-transfected cells respectively. The amount of cAMP-driven β-galactosidase expression in each well was assessed with a colorimetric assay measuring absorbance at 570 nm on a microplate spectrophotometer. Ligand-induced cAMP stimulation was expressed as a percentage of maximal response of H2 relaxin or INSL3 for RXFP1 and RXFP2 cells respectively. Each data point was measured in triplicate and each experiment conducted independently at least three separate times. Statistical differences in $pEC_{50}$ values were analyzed using one-way ANOVA coupled to Newman Keul's multiple comparison test for multiple group comparisons in GraphPad Prism 6. Results for cells transfected with RXFP1 and 7BP cells are shown in Table 2. The single chain B7-33 C11.23S peptide was also shown to be selective at RXFP1 over RXFP2 (FIG. 3).

TABLE 2

Ligand binding of relaxin-2 B chain peptide derivatives and stimulation of cAMP response by relaxin-2 B chain peptide derivatives. Values in log M[1].

| | RXFP1 | | 7BP |
|---|---|---|---|
| Ligand | Eu-H2 pKi (n ≥ 3) | cAMP pEC50 (n ≥ 3) | Eu-H2 pKi (n ≥ 3) |
| H2 relaxin | 8.96 ± 0.03 | 10.49 ± 0.09 | 8.97 ± 0.10 (6) |
| B1-29 C11.23S | <5 | <5 | — |
| B1-33ox | 6.61 ± 0.24# | <5 | — |
| B1-33 C11.23S | 5.33 ± 0.15# | 5.10 ± 0.06# | — |
| B7-33ox | 6.15 ± 0.15# | 5.11 ± 0.11# | — |
| B7-33 C11.23S | 5.54 ± 0.13# | 5.12 ± 0.06# | 7.65 ± 0.10# |
| B7-29 C11.23S | <5 | <5 | — |
| B7-33 C11.23S R17K | <5 | <5 | — |
| B7-33 C11.23S R17HR | 6.52 ± 0.07# | <5 | — |
| B7-33 C11.23S R17NR | <5 | 5.81 ± 0.15# | — |
| AcB7-33 C11.23S | 6.00 (n = 1) | 5.40 ± 0.04# | 7.54 ± 0.10# |
| R13A (AcB7-33 C11.23S) | <5 | <5 | 5.76 ± 0.19# |
| R17A (AcB7-33 C11.23S) | <5 | <5 | 6.01 ± 0.12# |
| R20A (AcB7-33 C11.23S) | <5 | <5 | — |
| R13/17A. I20A (AcB7-33 C11.23S) | <5 | <5 | 5.54 ± 0.18# |
| KKKK (AcB7-29 C11.23S) | 6.25 ± 0.01# | 5.81 ± 0.11# | 8.91 ± 0.08 | p < 0.001 vs H2 relaxin

[1]Data are presented as the mean ± S.E of the percentage of the total specific binding of triplicate wells, repeated in at least three separate experiments, and curves were fitted using one-site binding curves in GraphPad Prism 6 (GraphPad Inc, San Diego, CA).

Example 3

Stimulation of Signaling Pathways by B7-33 C11.23S

Figure 4:
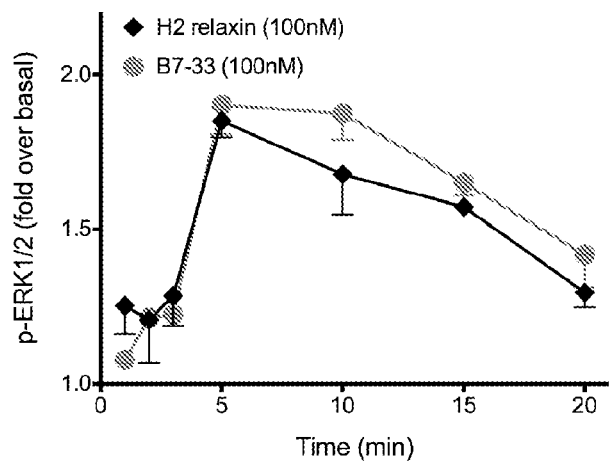
FIG. 4. Time course of ERK1/2 activation by H2 relaxin (H2 relaxin, diamonds) or B7-33 C11.23S (B7-33, circles) in rat renal myofibroblasts.

The inventors then tested the single chain B7-33 C11.23S relaxin-2 peptide for its ability to signal via different pathways, cAMP (see Example 2) and pERK.1/2 on HEK-293T (cells stably expressing RXFP1) and myofibroblast cells (cells endogenously expressing RXFP1) The cAMP assay was conducted as described in Example 2. Phosphorylation of ERK1/2 was determined using AlphaScreen SureFire® assay which is a proprietary, non-radioactive and non-Western proximity assay that relies on singlet oxygen energy transfer (PerkinElmer Inc.). Rat renal fibroblasts (that endogenously express RXFP1 receptor) were seeded into a 96-well plate at a density of 40,000 cells per well and incubated overnight in complete media to allow cell adhesion. Cells were then serum-starved for 4-6 hours followed by native H2 relaxin (100 nM) or B7-33 C11.23S peptide (100 nM) treatment for periods of up to 20 minutes and ERK1/2 activation was quantified using the phospho-ERK1/2 Surefire AlphaScreen kit. B7-33 C11.23S stimulated ERK1/2 with slightly higher level of efficacy as H2 relaxin peaking at 5 minutes following the peptide treatment (FIG. 4).

The inventors tested B7-33 in both stably-(HEK-293T) and natively-expressing (rat renal myofibroblast) RXFP1 cells. At first the peptide was tested in HEK-RXFP1 cells for its ability to activate cAMP (FIG. 3A) and EKR signalling pathways (data not shown) and was found to act as a full agonist, but with poor potency. Despite the poor potency in HEK-RXFP1 cells, when tested in rat renal myofibroblast it exhibited very high pERK potency (FIG. 4).

Example 4

In vitro Anti-fibrotic Activity of B7-33 C11.23S

The inventors then investigated the ability of the single chain B7-33 C11.23S relaxin-2 peptide to induce matrix metalloproteinase-2 (VIMP-2) activity, which provides a measure of the anti-fibrotic activity of the polypeptide.

Renal myofibroblast cells natively expressing human RXFP1 were plated out onto 12-well plates with a density of 50 000 cells per well. Cells were treated with 16.8 nM H2-relaxin and 16.80 nM B7-33 C11.23S. Expression of basal MMP-2 levels was monitored with no treatment applied to wells (control). Each treatment was carried out in duplicates (n=5), for each replicate in Dulbecco's modified Eagle's medium (DMEM) containing 10% fetal calf serum, 2.2% HEPES buffer, 1% L-glutamine and 2% penicillin/strepticillin. The cells were incubated over 48 hrs in a humidified chamber with 5% $CO_2$ at 37.8° C. temperature. Following this, media was aspirated off and experiment continued in serum free media (DMEM containing 2.2% HEPES buffer, 1% L-glutamine, 2% penicillin/strepicillin and 2% lactalbumin hydrolysate) for a further 24 hours in a humidified chamber with 5% $CO_2$ at 37.8° C. room temperature. Media were then collected from various treatments and gel zymography was carried out.

For determination of MMP-2 expression within various treatments, zymographic assays of gelatinases were carried out. Polyacrylamide separating gel containing 7.5% acrylamide, 0.35M Tris-Cl pH8.8, 0.4% SDS, 0.5 mg/ml gelatine solution (porcine skin, 300 bloom), was stacked below a polyacrylamide stacking gel containing 3.75% acrylamide, 0.25M Tris-Cl pH6.8, 0.4% SDS. Media from various treatments were incubated with gel loading sample buffer (0.0625M Tris-HCl, pH6.8, 2% SDS, 10% glycerol, 0.01% bromophenol blue) in 1:4 dilution at room temperature for 1 hr. 25 µL of various samples were applied to gel lanes. Gels are run at 200V constant voltage till the dye front nears the end of the gel. The completed gels were separated from the glass plates and washed twice (15 min per wash) in 0.25% Triton X-100 (to remove SDS from the gel proteins). The gels were incubated overnight (>16 hours) with incubation buffer at 37° C. (0.05M Tris-HCl pH 7.4, 0.01M $CaCl_2$, 5% Triton X-100, 0.02% sodium azide, 1 µM $ZnCl_2$. The gels were then stained with 0.1% Cootnassie blue containing 40% 2-propanol and destained with 7% acetic acid before analysed by ImageJ software.

Figure 5:
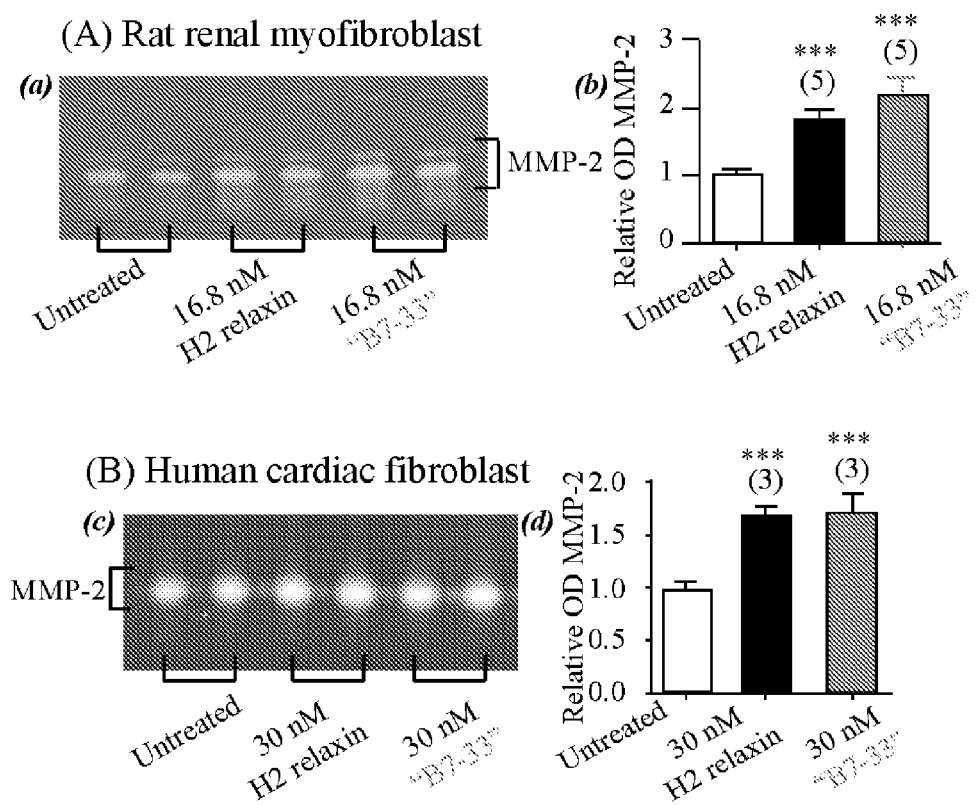
FIG. 5. Single chain B7-33 C11.23S peptide (B7-33) promotes expression of MMP-2 to similar levels as native H2 relaxin in both (A) rat renal myofibroblasts and (B) human cardiac fibroblasts, as demonstrated by gelatin zymography (a, c) and densitometry (b, d). Data shown (b and d) are mean±SEM (n=3-5 separate experiments). ***$p<0.001$ vs untreated control.

As shown in FIG. 5, the single chain B7-33 C11.23S relaxin-2 peptide was shown to induce the expression of MMP-2 in rat renal myofibroblasts and human cardiac fibroblasts to levels similar to those induced by the native H2 relaxin. It is therefore concluded that the B7-33 C11.23S relaxin-2 peptide has similar anti-fibrotic properties as native H2 relaxin.

Example 5

In Vivo Anti-fibrotic Activity of B7-33 C11.23S

To determine the effect of the single chain B7-33 C11.23S relaxin-2 peptide on fibrosis in vivo, the inventors used a rat model of myocardial infarction, a mouse model of isoproterenol-induced heart failure, and a mouse model of chronic allergic airways disease (AAD).

Rats

Adult male Sprague-Dawley rats weighing 250-320 g were obtained from Animal Resources Centre, Perth, Wash., Australia. The rats were group housed in a constant temperature of 22±1° C. and a relative humidity of 50-60% under a controlled light-dark cycle of 12 hours. Rats were given access to standard laboratory rat chow and drinking water ad libitum.

All procedures were approved by the Florey Institute Animal Ethics Committee and were performed in accordance with the Prevention of Cruelty to Animals Act, Australia 1986 and conformed with guidelines set out by the National Health and Medical Research Council of Australia (2007).

Mice

Seven to eight-week old male 129SV mice (which are sensitive to tissue injury and fibrosis) and age-matched female Balb/c mice (which are sensitive to changes in airway hyperresponsiveness) were used for the induction of isoproterenol-induced cardiomyopathy and ovalbumin-induced chronic allergic airways disease, respectively. 16 five week-old male C57BL/6 mice were used in the induction of prostate cancer growth. All animals were obtained from Monash Animal Services (Monash University, Clayton, Victoria, Australia) and housed under standard conditions (maintained on an 12 h light-12 h dark lighting cycle with free access to food and water) in the Department of Pharmacology Animal Room at Monash University.

All animals were given at least 5 days to acclimatize before any experimentation was conducted on them. All procedures were approved by Monash University's Animal Ethics Committees, which adhere to the Australian Code of Conduct for care and use of laboratory animals for scientific purposes.

Measurement of Airway Hyperresponsiveness

Twenty-four hours after the last vehicle/drug administration, methacholine-induced airway reactivity was assessed by invasive plethysmography as described before (Locke et al. 2007, *Am J Respir Mol Biol* 36, 625-632; Royce et al. 2009, *Endocrinology* 150, 2692-2699). Mice were anaesthetized intraperitoneally with 200 µg/g ketamine and 10 µg/g xylazine. Tracheotomy was performed using an 18-gauge tracheotomy tube and jugular vein cannulated with a 0.61 9 0.28 mm polyethylene tube (Microtube Extrusions, North Rocks, NSW, Australia), Mice were then placed in a plethysmograph chamber (Buxco Research Systems, Wilmington, N.C., USA) where increasing concentrations of acetyl-β-methacholine (from 31.25 µg/kg to 500 µg/kg) were delivered intravenously in five doses. After every dose, airway resistance and compliance were measured (Biosystem XA version 2.7.9; Buxco Electronics Inc, Wilmington, N.C., USA). The change in airway resistance calculated by the maximal resistance after each dose minus baseline resistance (phosphate buffered saline alone) was plotted against each dose of methacholine evaluated.

Histopathology

The mid zone of the male mouse heart and largest lung lobe from female Balb/c mice were fixed in 10% neutral buffered formalin for 24-48 h before being processed and embedded routinely in paraffin wax. Representative sections of tissue, 3-5 um each, were taken and stained with either picrosirius red (Samuel et al. 2011 *Lab Invest* 91, 675-690) for the detection of interstitial collagen or Masson's trichrome (Royce et al, 2009, *Endocrinology* 150, 2692-2699) for the detection of subepithelial basement membrane collagen deposition).

Morphometric Analysis of Structural Changes

Changes in picrosirius-red stained interstitial collagen or epithelial thickness and subepithelial collagen (fibrosis) around the airway lumen from Masson's trichrome-stained sections; which were all captured (at ×20 magnification) using a SPOT digital camera (Q Imaging, Burnaby, BC, Canada) and analysed with Image J 1.3 software (National Institutes of Health, Bethesda, Md.). Four to five fields per mid zone of the heart or 4-5 airways (of 150-350 µm in diameter) per mouse were assessed. Epithelial thickness and subepithelial collagen regions were traced with a digital pen and the thickness of each region calculated by the imaging software. Results were expressed as mean thickness (1 µm) of the 4-5 airways sampled.

Hydroxyproline Analysis

The apical region of the heart or second largest lung lobe from each mouse was treated as described previously (Samuel C S, et at., 2003, *FASEB J* 17, 121-123; Royce et at. 2009, *Endocrinology* 150, 2692-2699) for the determination of hydroxyproline content. Hydroxyproline values were estimated based on a standard curve constructed with serial dilutions of a 0.1 mg/mL stock of trans-4-hydroxy-proline-L-proline (Sigma-Aldrich). Hydroxyproline values were then converted to collagen content as detailed previously (Samuel CS, et al. 2004. *Endocrinology* 145, 4125-4133) and, in turn, divided by the dry weight of each corresponding left ventricular or lung tissue assessed to yield collagen concentration (a measure of fibrosis).

Statistical Analysis

All data were expressed as the mean+/−SEM and analysed using GraphPad Prism 6 (GraphPad Software Inc., San Diego, Calif., USA). The results were analysed by one-way ANOVA, using the Newman-Keuls post hoc test for multiple comparisons between treatment groups in all experiments performed except for the analysis of the lung function (AHR) data, which was assessed by a two-way ANOVA with Bonferroni's post hoc test. P<0.05 was considered to be statistically significant.

Myocardial Infarction-induced Heart Failure

Heart failure was induced as previously described (Ruchaya et al., 2014, *Exp Physiol* 99, 111-122). Breifly, to induce heart failure, rats were anaesthetised with an intramuscular injection of ketamine (60 mg/kg) and medetomide hydrochloride (250 mg/kg). A left sided thoracotomy through an opening between the fourth and fifth rib was performed, the heart was exteriorised and the left anterior descending coronary artery was ligated. Anaesthesia was reversed with antipamezole hydrocholide (1 mg/kg). Penicillin (1000 U) and buprenorphine (0.05 mg/kg) was administered to aid post-operative recovery. Animals were left to recover from the surgery under a heating source. Rats were individually housed after the surgery.

Eight weeks after myocardial infarction surgery, rats were randomly assigned to 3 groups (vehicle, H2 and B7-33), re-anaesthetised (2-3% isoflurane) and an osmotic minipump (model 2ML4, Alzet, Cupertino, Calif.) implanted intraperitoneally. Vehicle (saline), native H2 relaxin (0.5 mg/kg/day) or B7-33 C11.23S (0.5 mg/kg/day) was continuously administered for 28 days. At the conclusion of treatment, rats were anaesthetized (sodium pentobarbitone, 60 mg/kg i.p.) and the left ventricular end-diastolic pressure determined prior to decapitation and removal of the heart for histological analysis.

Figure 6:
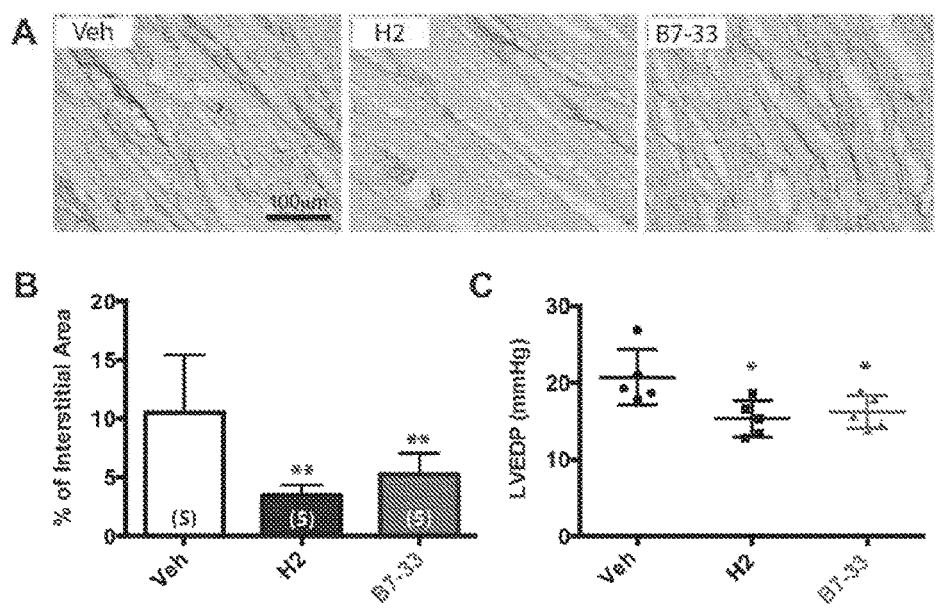
FIG. 6. Effect of H2 relaxin and B7-33 C11.23S peptide (B7-33) treatment on cardiac fibrosis and function in a rat model of myocardial infarction. Picrosirius red stained left ventricles of the heart from vehicle (Veh). H2 relaxin (1-12) and B7-33 C11.23S treated rats (A). H2 relaxin and B7-33 C11.23S significantly reduce the percentage of collagen in the interstitial area compared with vehicle treated rats (B). Left ventricular end-diastolic pressure (LVEDP) is reduced in animals treated with H2 relaxin and B7-33 C11.23S compared to vehicle-treated animals 12 weeks after myocardial infarction (C). **$p<0.01$ vs control group; *$p<0.05$ vs control group.

Rats treated with either H2 relaxin or B7-33 C11.23S demonstrated a significant reduction in percentage of collagen in the interstitial area of the left ventricle as compared with vehicle-treated animals (FIG. 6A, B). Left ventricular end-diastolic pressure (LVEDP) was also reduced in H2 relaxin or B7-33 C11.23S treated animals (FIG. 6C), indicating that both H2 relaxin and B7-33 C11.23S treatment promote a similar improvement in heart function 12 weeks following myocardial infarction.

Isoproterenol-induced Cardiomyopathy

Male 129SV mice were subcutaneously injected with isoprenaline hydrochloride (25 mg/kg; Sigma-Aldrich) once daily for 5 consecutive days and then left for a further 9 days for fibrosis progression to occur. Subgroups of animals (n=7-8/group) received no treatment (injury alone control) or recombinant H2 relaxin (0.5 mg/mg/day; a dose that had been used previously to successful demonstrate its anti-fibrotic actions (Samuel C S, et at. 2004, *Endocrinology* 145, 4125-4133; Samuel et al. 2011 *Lab Invest* 91, 675-690) and produce circulating levels of 20-40 ng/ml (Samuel CS, et al., 2003, *FASEB J* 17, 121-123), which are well within those found in pregnant rodents). Alternatively, an equivalent dose of the B7-33 peptide (0.25 mg/mg/day corrected for MW) was administered via subcutaneously implanted osmotic minipumps model 2002; Alzet, Cupertino, Calif.), which allowed for the continuous infusion of each peptide into the circulation of treated animals. A separate subgroup of mice (n=7) that were not subjected to isoproterenol or peptide treatment were used as untreated controls. Nine days after the fifth isoproterenol injection/14 days from the beginning of the study, all mice were weighed and then sacrificed for heart and left ventricular collection. A similar portion of the left ventricle from each animal was then used for the determination of interstitial collagen staining and morphometric analysis of interstitial collagen density (Samuel et al. 2011 *Lab Invest* 91, 675-690) or hydroxyproline content (Samuel C S, et al. 2004, *Endocrinology* 145, 4125-4133).

Figure 7:
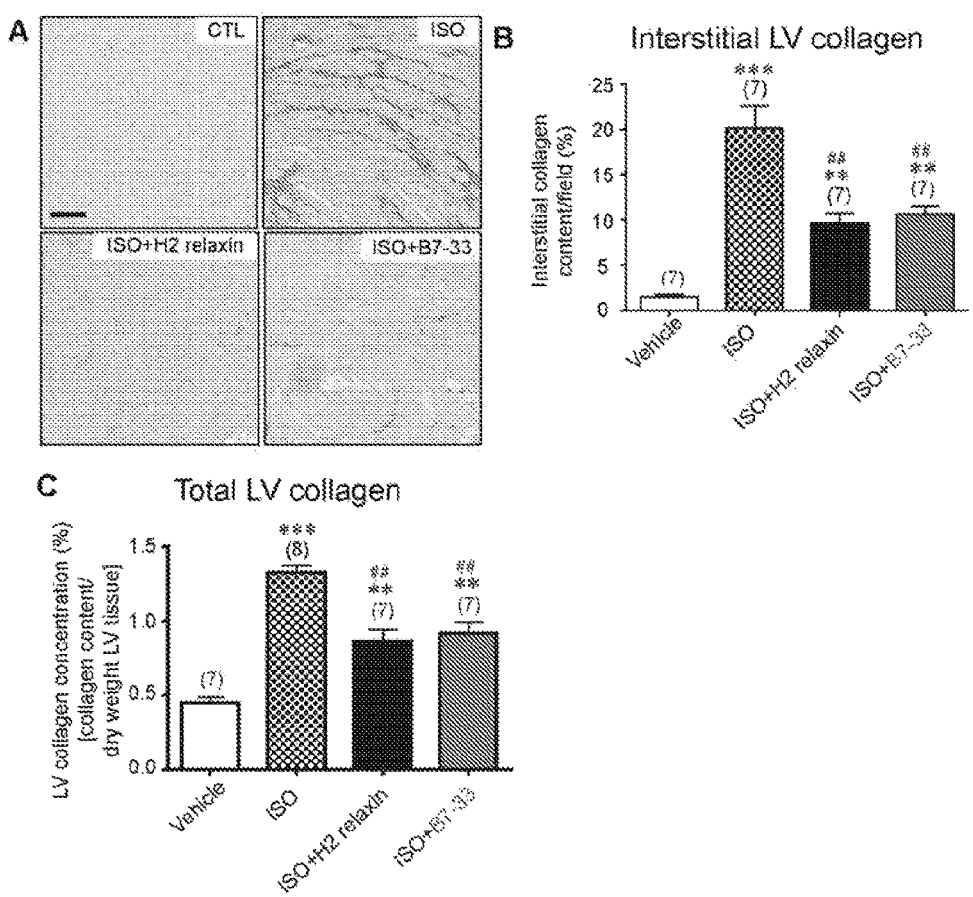
FIG. 7. Effect of H2 relaxin and B7-33 C11.23S peptide (B7-33) treatment on cardiac fibrosis in a mouse model of isoproterenol (ISO) induced cardiac fibrosis. Picrosirius red stained left ventricles of the heart from vehicle, ISO, ISO and H2 relaxin, and ISO and B7-33 C11.23S treated mice (A). Percentage interstitial collagen content, determined by picrosirius red staining (B), and total left ventricular collagen concentration, determined by hydroxyproline analysis (C) demonstrate that ISO significantly increases left ventricular collagen density and concentration. The ISO-related increase in collagen is reduced by treatment with H2 relaxin or B7-33 C11.23S. $p<0.01$, *$p<0.001$ vs control group, ##$p<0.01$ vs ISO group.

At 14 days, the isoproterenol-treated group displayed a significant elevation in both percentage of interstitial collagen (FIG. 7A, B) and total collagen concentration (FIG. 7C) in the left ventricle. Treatment with H2 relaxin or B7-33 C11.23S significantly reduced the collagen percentage and total concentration to a similar extent relative to isoproterenol treatment (FIGS. 7B and 7C) suggesting that B7-33 C11.23S has similar anti-fibrotic properties to H2 relaxin.

Induction of Chronic Allergic Airway Disease

The inventors also tested the fibrosis preventing activity of B7-33 C11.23S in a model of chronic allergic airway disease (AAD). A chronic model of ovalbumin (OVA)-induced AAD (Temelkovski et al. 1998, *Thorax* 53, 849-856) was established in female Balb/c mice (n=40). Mice were sensitized i.p. on day 0 and 14 with 10 μg Grade V chicken egg ovalbumin (Sigma-Aldrich Corp., St. Louis, Mo., USA) and 0.4 mg aluminium potassium sulphate (alum) in 0.5 mL saline, then challenged by whole body inhalation exposure to aerosolized 2.5% OVA (weight/volume of saline) three times a week from days 21-63 (30 min per session) using an ultrasonic nebulizer (Locke et al. 2007, *Am J Respir Cell Mol Biol* 36, 625-632). Control mice (n=14) were sensitised with 0.4 mg albumin 0.5 mL saline and challenged with nebulised saline.

Figure 8:
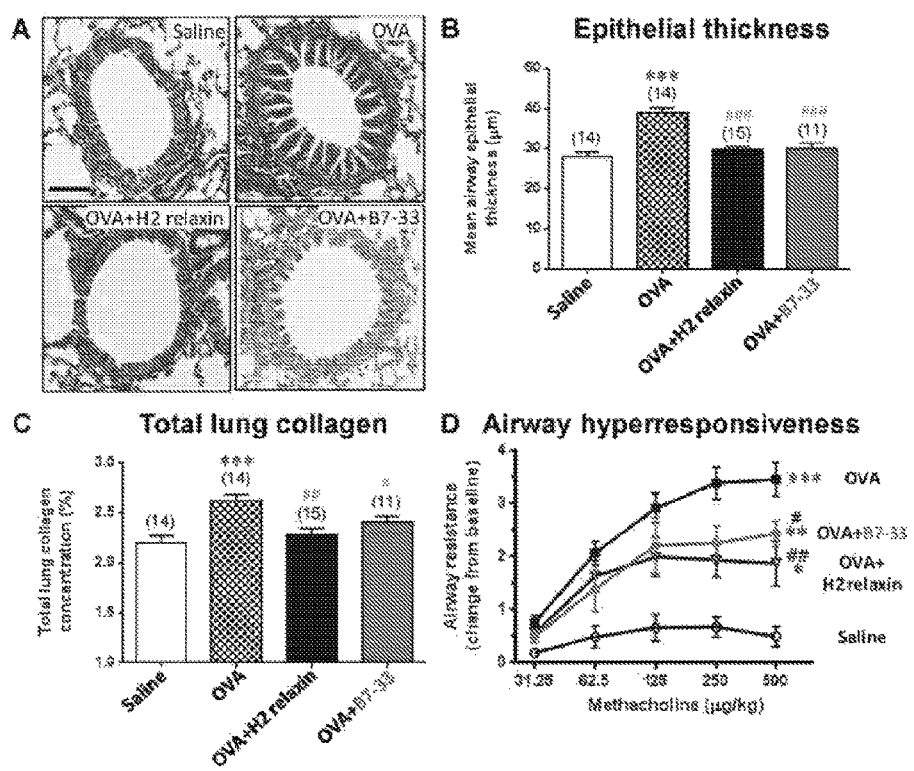
FIG. 8. Effect of H2 relaxin and B7-33 C11.23S peptide (B7-33) treatment on measures of fibrosis in a mouse model of OVA-induced chronic allergic airway disease. Masson trichrome-stained lung airway sections of vehicle, OVA and vehicle, OVA and H2 relaxin, and OVA and B7-33 C11.23S treated mice (A), scale bar=300 µm. H2 relaxin and B7-33 C11.23S normalise subepithelial collagen thickness (µm) in the lamina reticularis after treatment with OVA (B). Total lung collagen content (a measure of fibrosis), measured by hydroxyproline ananlysis, is also normalised in the H2 relaxin and B7-33 C11.23S treated groups relative to OVA treatment (C). Airway resistance measured in saline, OVA and vehicle, OVA and H2 relaxin and OVA and B7-33 C11.23S groups in response to increasing concentrations of the bronchoconstrictor, methacholine, by invasive plethysmography. Error bars represent SEM. ***$p<0.001$ vs control group, #$p<0.05$, ##$p<0.01$, ###$p<0.001$ vs OVA group.

Mean airway epithelial thickness was significantly increased by OVA treatment relative to vehicle treated animals (FIGS. 8A and 8B). Epithelial thickness was significantly reduced in animals treated with H2 relaxin or B7-33 C11.23S as compared to OVA treatment, with H2 relaxin or B7-33 C11.23S administration reducing epithelial thickness to levels similar to that of vehicle treatment (FIG. 8B). Similarly, total lung collagen concentration was elevated in OVA treated animals relative to vehicle treated controls and peptide treatment following OVA treatment reduced lung collagen relative to OVA alone (FIG. 8C). Thus the inventors demonstrate that H2 relaxin and B7-33 C11.23S have similar efficiencies in reducing structural changes associated with fibrosis. Functionally, OVA significantly elevates airway hyper-responsiveness as measured by changes in airway resistance and this increase is attenuated with H2 relaxin or B7-33 C11.23S treatment (FIG. 8D).

Thus B7-33 C11.23S has similar, albeit slightly diminished biological activity to that of H2 relaxin in the prevention of fibrosis and improvement of function in the heart and lung following chronic and acute disorders of these systems.

Example 6

B7-33 C11.23S Does Not Promote Prostate Tumour Growth

H2 relaxin can induce prostate and other tumour growth. To measure the effect of B7-33 C11.23S on tumour growth, 16 five week-old male C57BL/6 mice (obtained from Monash Animal Services) were injected with 5000 RM1 (mouse prostate tumor) cells into their prostates to induce tumor growth. One sub-group of mice n=5 was left untreated until day 10 post-RM1 cell administration. Additional sub-groups of mice were subcutaneously implanted with osmotic mini-pumps (model 1007D, Durect Corp., Cupertino, Calif., USA) containing H2 relaxin alone (0.15 mg/kg/day; n=5) or B7-33 C11.23S (0.075 mg/kg/day; corrected for MW; n=6) on day 2 post-RM1 cell administration and maintained until day 10 post-cell administration. Each pump had a reservoir that allowed it to continuously infuse the peptides administered to mice for 8 days.

Figure 9:
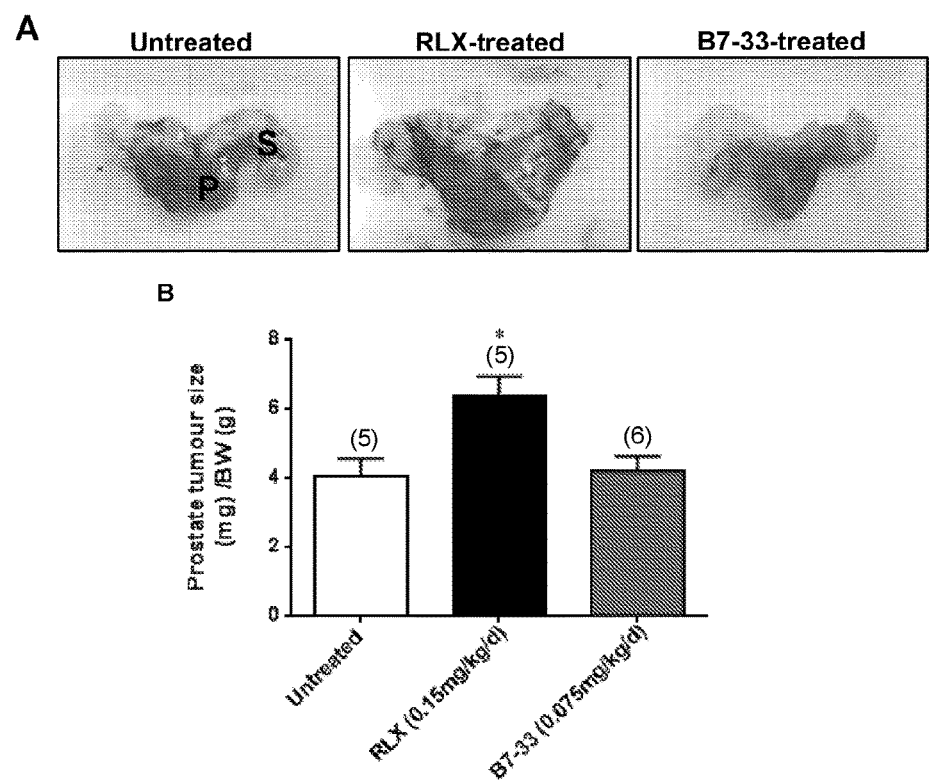
FIG. 9. Tumour development 10 days after injection with 5000RM1 mouse prostate tumour cells into prostates of C57B6J mice (A). Tumour development was promoted by H2 relaxin, but not B7-33 C11.23S peptide (B7-33) (B). *$p<0.05$ vs untreated. SV: seminal vesicle, PT: prostate tumour.

H2 relaxin significantly increased tumour size compared to tumours of untreated mice (FIG. 9). B7-33 C11.23S treatment did not result in changes in tumour size relative to untreated, and tumours from B7-33 C11.23S treated mice were significantly smaller than those from H2 relaxin treated mice (FIG. 9) suggesting that B7-33 C11.23S may be a safer option than H2 relaxin for therapeutic administration.

The invention claimed is:

1. A single chain relaxin peptide having relaxin-2 activity comprising a relaxin B chain derived from relaxin-2, wherein the peptide is truncated by six amino acid residues at the N-terminus with respect to the sequence of the B chain of native relaxin-2 shown in SEQ ID NO: 1, wherein the peptide comprises four additional amino acids at the C-terminus, at least two of which are positively charged, and wherein one or both cysteine residues at positions 11 and 23, with respect to the native human relaxin-2 B chain sequence of SEQ ID NO: 1, is replaced with a neutral amino acid.

2. A peptide according to claim 1, wherein the additional amino acids at the C-terminus comprise KRSL (amino acid residues 30-32 of SEQ ID NO: 3).

3. A peptide according to claim 1, wherein one or both cysteine residues at positions 11 and 23 is replaced with serine or alanine.

4. A single chain relaxin peptide having relaxin-2 activity comprising a relaxin B chain derived from relaxin-2, wherein the peptide is truncated by six amino acid residues at the N-terminus with respect to the sequence of the B chain of native relaxin-2 shown in SEQ ID NO: 1. wherein the peptide comprises four additional amino acids at the C-terminus, at least two of which are positively charged, and wherein one or both cysteine residues at positions 11 and 23, with respect to the native human relaxin-2 B chain sequence of SEQ ID NO: 1, is replaced with a neutral amino acid, wherein one or more arginine residues of the native human relaxin-2 B chain sequence are replaced by a basic amino acid.

5. A peptide according to claim 4, wherein the basic amino acid is lysine, or a mimetic or isostere of arginine.

6. A peptide according to claim 5, wherein said mimetic or isostere is homoarginine, norarginine or guanidine propionic acid.

7. A peptide according to claim 4, wherein the arginine residue at position 17 of the native human relaxin-2 B chain sequence shown in SEQ ID NO: 1 is replaced by lysine, homoarginine, norarginine or guanidine propionic acid.

8. A peptide according to claim 1, wherein the peptide comprises or consists of the amino acid sequence shown in any one of SEQ ID NO: 7, 9, 10 or 11.

9. A peptide according to claim 1, wherein the peptide comprises a C-terminal amide group and/or an N-terminal acetyl group.

10. A peptide according to claim 1, wherein the peptide is selective for the RXFP1 receptor.

11. A peptide according to claim 1, wherein the peptide is an agonist of the RXFP1 receptor.

12. A polynucleotide encoding a single chain relaxin peptide according to claim 1.

13. A pharmaceutical composition comprising a single chain relaxin peptide according to claim 1, optionally together with one or more pharmaceutically acceptable carriers, excipients or diluents.

14. A composition comprising a polynucleotide of claim 12, optionally together with one or more pharmaceutically acceptable carriers, excipients or diluents.

* * * * *